United States Patent [19]

Wannag

[11] 4,263,898

[45] Apr. 28, 1981

[54] VAGINAL SPECULUM

[76] Inventor: Arne T. Wannag, 11A Palnasvagen, 133 00 Saltsjobaden, Sweden

[21] Appl. No.: 156,444

[22] Filed: Jun. 4, 1980

Related U.S. Application Data

[63] Continuation of Ser. No. 917,830, Jun. 22, 1978, abandoned.

[30] Foreign Application Priority Data

Jun. 22, 1977 [SE] Sweden .............................. 7707282

[51] Int. Cl.³ .............................................. A61B 1/32
[52] U.S. Cl. .................................................... 128/17
[58] Field of Search .................................. 128/17–19, 128/3–5, 303.11, 303.12, 341, 345, 321–324, 361, 328, 242, 244, 346; 81/302, 501 R, 427, 428 R

[56] References Cited

U.S. PATENT DOCUMENTS

| | | | |
|---|---|---|---|
| 3,575,163 | 4/1971 | Gasper | 128/17 |
| 3,815,585 | 6/1974 | Fiore | 128/17 |
| 3,847,143 | 11/1974 | Cotey et al. | 128/17 |

FOREIGN PATENT DOCUMENTS 365707  4/1974  Sweden .................................. 128/17

*Primary Examiner*—Robert W. Michell
*Assistant Examiner*—C. W. Shedd
*Attorney, Agent, or Firm*—William A. Drucker

[57] ABSTRACT

A disposable one-piece vaginal speculum is self-holding in various opening positions of the blades of the speculum by means of integral latching mechanism and the speculum has handle portions to be grasped by one hand and being located outside the visual field through the speculum but in such vicinity to said latching means that the latter may be manipulated by one of the fingers of the hand grasping the handle portions.

Preferably the latching mechanism comprises a resilient arcuate latching tongue having a plurality of latching teeth each being engageable with a tooth of one of the handle portions.

1 Claim, 2 Drawing Figures

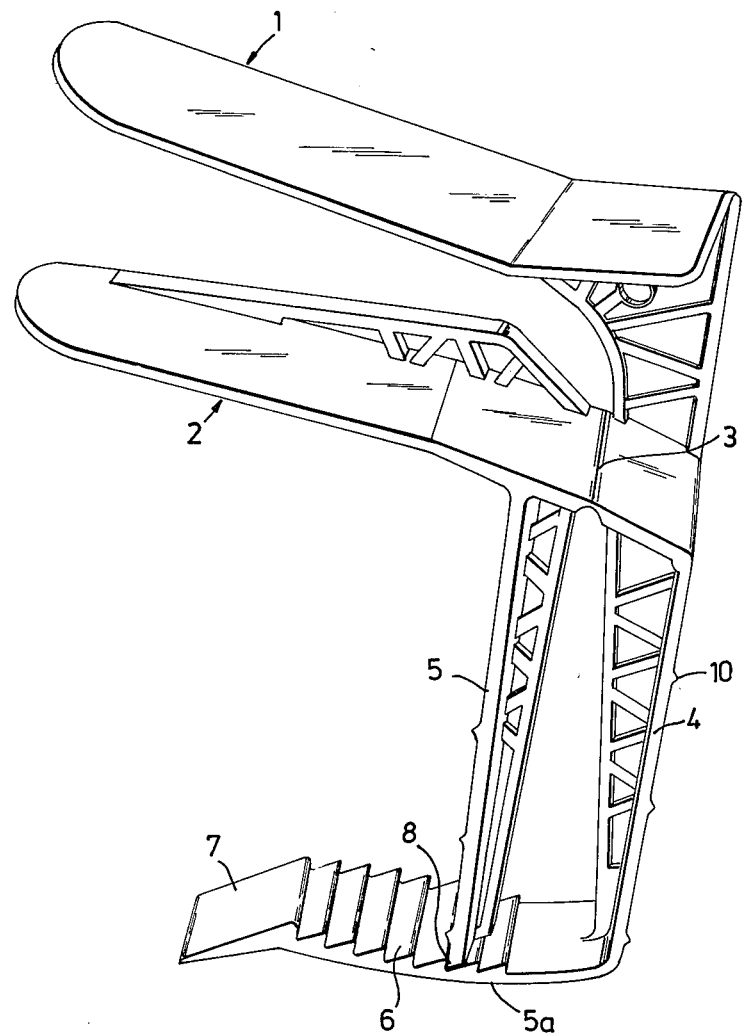

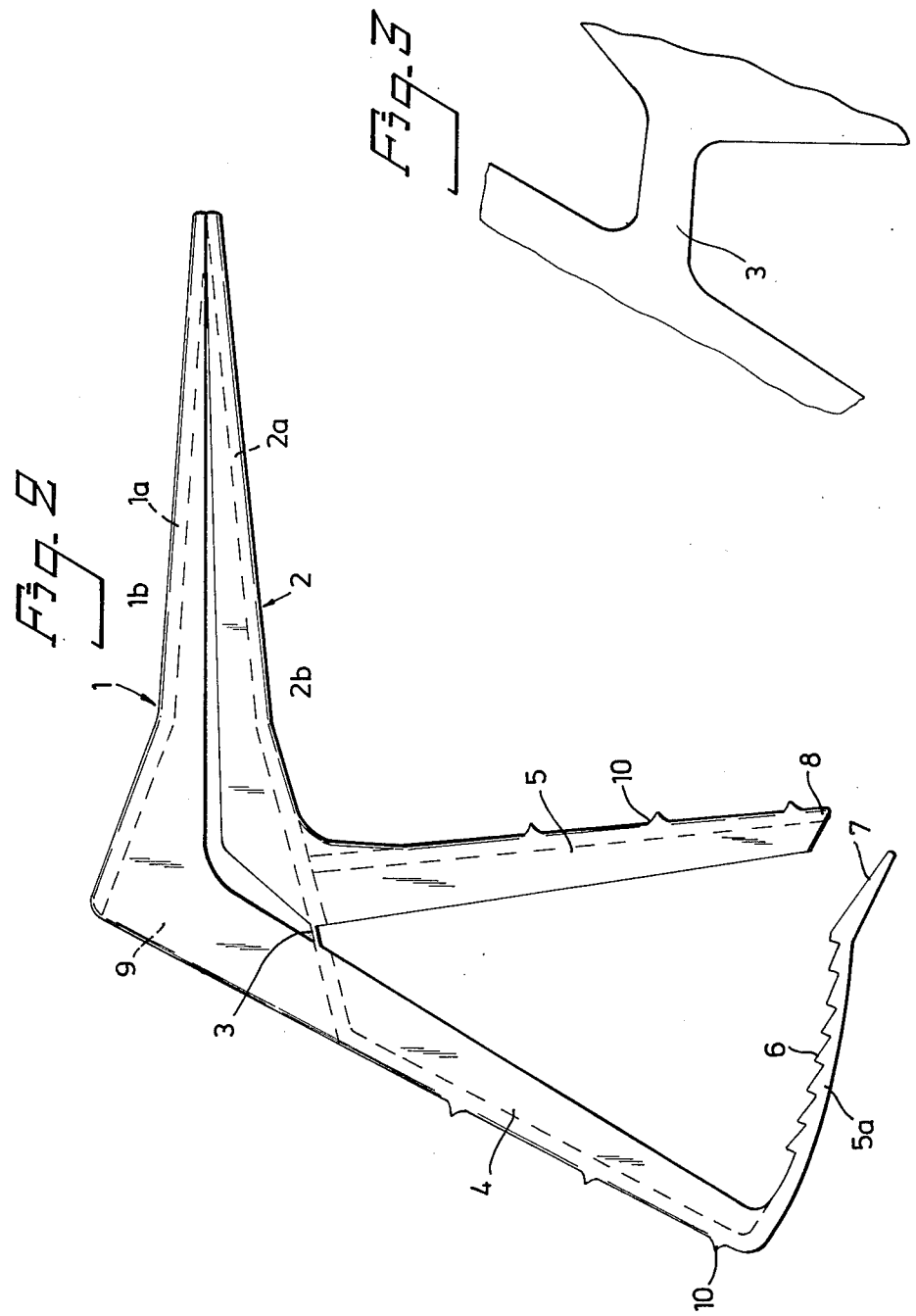

VAGINAL SPECULUM

This is a continuation of my U.S. Pat. application Ser. No. 917,830 filed June 22, 1978, now abandoned.

BACKGROUND OF THE INVENTION

This invention refers to a surgical instrument, a speculum, for examining body orifices or cavities and more particularly to a vaginal speculum of simple construction providing a wide range of adjustability and ease of operation and manipulation. The speculum can be inexpensively made in one piece molded from plastic and economically permits disposal of the speculum after use.

The primary improvement over specula known in the art is in providing handle portions located outside the visual field through the speculum and adjacent to a releasable latching means. In this invention the speculum is self-holding in various opening positions and the opening of the blades of the speculum as well as the release of the latching action is performed by the hand grasping the handle portions.

SUMMARY OF THE INVENTION

Accordingly a primary object of the present invention resides in the provision of an improved disposable speculum of simple one-piece construction.

An additional object resides in in the provision of an improved speculum of simple construction providing reliability and ease of access through the speculum and adjustments during use.

Still another resides in the provisions of an improved one-piece speculum incorporating plural latching adjustments, control and manipulation as well as releasing the latching action being readily performed with one hand by the operator.

Futher novel features and other objects of this invention will become apparent from the following detailed description and appended claims taken in conjunction with the accompanying drawings showing a preferred structure and embodiment, in which:

BRIEF DESCRIPTION OF THE DRAWINGS

FIG. 1 is a perspective view of the improved speculum with the blades thereof separated, i.e. located in an operative position.

FIG. 2 is a side view of the speculum in the inoperative position thereof with the blades brought together; and FIG. 3 shows on an enlarged scale the part of the speculum which serves as a hinge.

The new speculum has a first blade 1 and a second blade 2. Said blades are pivotally connected to each other by means of a hinge 3 and each one merges into a handle portion 4 and 5, respectively.

One of said handle portions 4 has an arcuate resilient portion 5a, having a plurality of latching teeth 6. The arcuate portion 5a terminates in an oblique entering portion 7.

The free end of the other handle portion 5 is shaped as a latching tooth 8 which is so formed that it may latchingly engage the latch ing teeth 6 of the arcuate portion 5a. The blades 1 and 2 have a section which is of substantially U-shape, the web portions 1a and 2a, respectively being so positioned relative to each other so that when the blades are separated from each other a through passage 9 is defined, extending in the longitudinal direction of the blades and permitting observation between the blades and also into the area defined by the ends of the blades.

The inner surfaces of the flanges 1b, 2b of the blades thereby define guiding means for instruments intended to be used by the examination or treatment.

Also the handle portions are preferably shaped as U-beams or the like thereby offering—as well as the blades 1,2—a great resistance against bending.

In order to facilitate the manipulation of the speculum and prevent the hand from sliding both portions 4,5 of the handle preferrably have ridges 10 or similar means. The vaginal speculum is preferably made from a plastic material having a limited so called hinge-effect. A rigid polyethylene may be mentioned as a suitable material as it permits approximately 100 bendings of a conveniently shaped hinge. FIG. 3 illustrates on a larger scale the thin connecting portion defining the actual hinge 3.

Despite the fact that the handle portions 4,5, as mentioned above, have a relatively great resistance against bending, they will however be bent to some extent, and since the load will substantially be exerted towards the parts of the handle portions which is directed away from the hinge point and the handle portions have a decreasing section towards said free ends, the two handle portions will bend or curve so that they present concave surfaces towards each other. Thus, the grip between the latching teeth 6 and the latching tooth 8 will be increased. Thus, an effective latching is obtained, but since the entering portion is easily accessable by the finger and the portion 5a is made resilient, it is understood that it is possible to avoid the snapping sound, inherent with known vaginal specula and giving the women a negative psychological impression, when the handle portions are brought towards each other as well as when releasing the latch.

Since the speculum may be made in one integral piece, it is understood that it may be manufactured at a low cost and thereby it may be made made as a disposable product permitting the hygienic advantages inherent in such a product.

I claim:

1. A vaginal speculum comprising a unitary structure made of a resiliently deformable material and including:
    (i) a first elongated blade having two ends and two lateral sides connecting said ends, a first handle portion extending from said blade at an angle thereto at a position adjacent to one end of said blade,
    (ii) a second elongated blade having two ends and a second handle portion extending therefrom at an angle thereto at a position adjacent to one end thereof,
    (iii) a flange attached at one lateral edge and extending substantially perpendicularly from said first handle at a spacing from said one end of said first blade, said one end of said second blade and a juxtaposed end of said flange being connected by a unitary flexible hinge, the portion of the first handle lying between the first blade and said flange being positioned at a lateral edge of said first blade such that upon moving said blades apart there is provided between said first blade and said second blade together with said flange and adjacent said first handle portion, an unimpeded channel for viewing from said one ends of the blades towards the other end of the blades, and (iv) an arcuate resilient tongue formed on a free end of one of said handle portions and inlcuding a plurality of latching teeth thereon, the free end of the other of said handle portions being formed as a latching tooth which engages with any one of said latching teeth of the one said handle portion said tooth and teeth being oriented in such fashion as to retain said handles so that said channel remains unimpeded.

* * * * *